United States Patent
Miz et al.

(10) Patent No.: US 11,033,301 B2
(45) Date of Patent: Jun. 15, 2021

(54) SPINAL IMPLANT AND METHODS OF USE THEREOF

(71) Applicant: K2M, Inc., Leesburg, VA (US)

(72) Inventors: George Miz, Palos Park, IL (US); Scott Koysh, Pittsburgh, PA (US)

(73) Assignee: K2M, Inc., Leesburg, VA (US)

( * ) Notice: Subject to any disclaimer, the term of this patent is extended or adjusted under 35 U.S.C. 154(b) by 141 days.

(21) Appl. No.: 16/341,287

(22) PCT Filed: Oct. 11, 2017

(86) PCT No.: PCT/US2017/056099
§ 371 (c)(1),
(2) Date: Apr. 11, 2019

(87) PCT Pub. No.: WO2018/071514
PCT Pub. Date: Apr. 19, 2018

(65) Prior Publication Data
US 2020/0289167 A1    Sep. 17, 2020

Related U.S. Application Data

(60) Provisional application No. 62/406,455, filed on Oct. 11, 2016.

(51) Int. Cl.
*A61B 17/70* (2006.01)

(52) U.S. Cl.
CPC ...... *A61B 17/7052* (2013.01); *A61B 17/7023* (2013.01); *A61B 17/7047* (2013.01);
(Continued)

(58) Field of Classification Search
CPC ............ A61B 17/7052; A61B 17/7023; A61B 17/7047; A61B 17/7056; A61B 17/7062; A61B 17/7079; A61B 17/7053
(Continued)

(56) References Cited

U.S. PATENT DOCUMENTS 5,383,392 A    1/1995  Kowalewski et al.
5,683,392 A   11/1997  Richelsoph et al.
(Continued)

FOREIGN PATENT DOCUMENTS

FR    2849590 A1    7/2004

OTHER PUBLICATIONS

International Search Report for Application No. PCT/US2017/056099 dated Jan. 8, 2018, 2 pages.
(Continued)

*Primary Examiner* — Eduardo C Robert
*Assistant Examiner* — David C Comstock
(74) *Attorney, Agent, or Firm* — Lerner, David, Littenberg, Krumholz & Mentlik, LLP

(57) ABSTRACT

A spinal rod connector includes first and second arm assemblies and a fastener. The first arm assembly includes a first base portion and a first head portion defining a first slot configured to receive a first spinal rod. The first base portion includes a hook and an extension member including a housing. The second arm assembly is adjustable with respect to the first arm assembly. The second arm assembly includes a second base portion including a hook, a second head portion defining a second slot configured to receive a second spinal rod, and an elongate member extending from the second base portion. The elongate member is configured to be received in the housing of the first arm assembly. The elongate member is rotatable about an axis offset from a longitudinal axis of the housing. The fastener is configured to be received in the housing to secure the elongate member.

21 Claims, 8 Drawing Sheets

(52) U.S. Cl.
CPC ...... *A61B 17/7056* (2013.01); *A61B 17/7062* (2013.01); *A61B 17/7079* (2013.01)

(58) Field of Classification Search
USPC .................. 606/279, 266, 270, 276, 277, 64
See application file for complete search history.

(56) References Cited

U.S. PATENT DOCUMENTS

| | | | |
|---|---|---|---|
| 5,707,372 | A | 1/1998 | Errico et al. |
| 5,733,286 | A | 3/1998 | Errico et al. |
| 6,238,396 | B1 * | 5/2001 | Lombardo ......... A61B 17/7052 606/251 |
| 6,589,243 | B1 | 7/2003 | Viart et al. |
| 7,658,582 | B2 | 2/2010 | Doubler et al. |
| 7,717,940 | B2 | 5/2010 | Woods et al. |
| 7,771,430 | B2 | 8/2010 | Jones et al. |
| 7,988,694 | B2 | 8/2011 | Barrus et al. |
| RE42,867 | E | 10/2011 | Hammill, Sr. et al. |
| 8,113,847 | B2 | 2/2012 | Boachie-Adjei |
| 8,162,991 | B2 | 4/2012 | Strauss et al. |
| 8,287,576 | B2 | 10/2012 | Barrus |
| 8,308,729 | B2 | 11/2012 | Nunley et al. |
| 8,337,532 | B1 | 12/2012 | McLean et al. |
| 8,361,122 | B2 | 1/2013 | Barrus et al. |
| 8,372,120 | B2 * | 2/2013 | James ................ A61B 17/7052 606/250 |
| 8,377,104 | B2 | 2/2013 | Jones et al. |
| 8,403,971 | B2 | 3/2013 | Barrus et al. |
| 8,506,603 | B2 | 8/2013 | McClintock et al. |
| 8,672,944 | B2 | 3/2014 | Boachie-Adjei et al. |
| 8,696,718 | B2 | 4/2014 | Barrus et al. |
| 8,714,427 | B2 | 5/2014 | McClintock et al. |
| 8,764,756 | B2 | 7/2014 | Jones |
| 8,814,919 | B2 | 8/2014 | Barrus et al. |
| 8,834,474 | B2 | 9/2014 | Jones et al. |
| 8,882,817 | B2 | 11/2014 | Jones et al. |
| 8,945,189 | B2 | 2/2015 | Barrus et al. |
| 8,961,523 | B2 | 2/2015 | Barrus et al. |
| 8,979,898 | B2 | 3/2015 | Ark et al. |
| 9,023,087 | B2 * | 5/2015 | Frankel .............. A61B 17/7037 606/308 |
| 9,125,703 | B2 | 9/2015 | McClintock et al. |
| 9,247,969 | B2 | 2/2016 | Nunley et al. |
| 9,675,386 | B2 | 6/2017 | Akbarnia et al. |
| 10,307,186 | B2 * | 6/2019 | Schafer .............. A61B 17/8869 |
| 10,667,852 | B2 * | 6/2020 | Shoshtaev ........... A61B 17/842 |
| 2002/0007183 | A1 | 1/2002 | Lee et al. |
| 2002/0143330 | A1 | 10/2002 | Shluzas |
| 2006/0241598 | A1 | 10/2006 | Khalili |
| 2007/0016189 | A1 | 1/2007 | Lake et al. |
| 2007/0016197 | A1 | 1/2007 | Woods et al. |
| 2008/0015588 | A1 * | 1/2008 | Hawkes ............. A61B 17/7052 606/64 |
| 2009/0292308 | A1 | 11/2009 | Jones et al. |
| 2011/0152934 | A1 | 6/2011 | Asaad |
| 2012/0130373 | A1 * | 5/2012 | Larroque-Lahitette ..................... A61B 17/7022 606/74 |
| 2012/0226316 | A1 | 9/2012 | Dant et al. |
| 2014/0257397 | A1 | 9/2014 | Akbarnia et al. |
| 2014/0316468 | A1 | 10/2014 | Keiser et al. |
| 2015/0320448 | A1 * | 11/2015 | Legallois ............ A61B 17/705 606/254 |
| 2016/0058478 | A1 | 3/2016 | Agarwal et al. |
| 2016/0157896 | A1 * | 6/2016 | Palmer ............... A61B 17/7041 606/278 |
| 2017/0303970 | A1 * | 10/2017 | Puryear ............. A61B 17/7032 |

OTHER PUBLICATIONS

European Search Report for Application No. 17860758.6, dated May 19, 2020, 9 pages.

* cited by examiner

SPINAL IMPLANT AND METHODS OF USE THEREOF

CROSS-REFERENCE TO RELATED APPLICATION

This application is a national phase entry under 35 U.S.C. § 371 of International Application No. PCT/US2017/056099, filed on Oct. 11, 2017, which claims priority to, and the benefit of, U.S. Provisional Patent Application Ser. No. 62/406,455, filed on Oct. 11, 2016, the entire contents of which are incorporated by reference herein

BACKGROUND

1. Technical Field

The present disclosure relates to an instrument for spinal surgery and, more particularly, to a surgical instrument for securing spinal rods.

2. Discussion of Related Art

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and spinal rods.

Securing the spinal rods using bone screws on a vertebra that may be too small, too fragile, or damaged to secure a bone screw thereon may be problematic. Furthermore, the use of bone screws also requires a substantial amount of work, time, and hardware during a surgical procedure.

Therefore, a continuing need exists for an improved device and a method for securing spinal rods to bone.

SUMMARY

In accordance with an embodiment of the present disclosure, there is provided a spinal rod connector including a first arm assembly, a second arm assembly, and a fastener. The first arm assembly includes a first base portion and a first head portion defining a first slot configured to receive a first spinal rod therein. The first base portion includes a hook portion and an extension member including an engagement housing defining a longitudinal axis. The second arm assembly is selectively adjustable with respect to the first arm assembly. The second arm assembly includes a second base portion, a second head portion defining a second slot configured to receive a second spinal rod therein, and an elongate member extending from the second base portion. The second base portion includes a hook portion. The elongate member is configured to be selectively received in the engagement housing of the first arm assembly. The elongate member is rotatable about a second axis offset from the longitudinal axis of the engagement housing. The fastener is configured to be received in the engagement housing to secure the elongate member of the second arm assembly thereto.

In an embodiment, the first arm assembly may include a stem configured to rotatably couple the first head portion with the first base portion. In particular, the stem may include a threaded portion threadably engaging the first base portion, and a ball portion rotatably coupled with the first head portion.

In another embodiment, the engagement housing of the first arm assembly may define apertures dimensioned to receive the elongate member of the second arm assembly. The apertures of the engagement housing of the first arm assembly may be dimensioned larger than a diameter of the elongate member. In particular, the apertures may have a conical profile.

In yet another embodiment, the engagement housing of the first arm assembly may include a ball defining a bore dimensioned to receive the elongate member of the second arm assembly.

In still yet another embodiment, the engagement housing may define an opening in registration with the ball. The opening may be configured to threadably receive the fastener configured to engage the ball to secure the elongate member of the second arm assembly with the engagement housing.

In still yet another embodiment, the first and second base portions may define engagement bores configured to engage an insertion instrument.

In an embodiment, at least one of the first or second slots may have a U-shaped profile.

In yet another embodiment, at least one of the first or the second head portions may be configured to threadably engage a set screw to secure the first or second spinal rod received in the first or second slot.

In accordance with another embodiment of the present disclosure, there is provided a spinal rod connector including a first arm assembly, a second arm assembly, and a fastener. The first arm assembly includes a first base portion including a hook portion and an extension member including an engagement housing. The first base portion defines a first fixation channel dimensioned to receive a first band configured to secure a first spinal rod to the first base portion. The second arm assembly is selectively adjustable with respect to the first arm assembly. The second arm assembly includes a second base portion including a hook portion, and an elongate member extending from the second base portion. The second base portion defines a second fixation channel dimensioned to receive a second band configured to secure a second spinal rod to the second base portion. The elongate member is configured to be selectively received in the engagement housing of the first arm assembly. The fastener is configured to be received in the engagement housing to secure the elongate member of the second arm assembly thereto.

In an embodiment, at least one of the first or second base portions may define apertures in communication with the first or second fixation channel.

In another embodiment, the apertures of the at least one of the first or second base portions may be orthogonal to each other.

In yet another embodiment, the elongate member of the second arm assembly may be movable through the engagement housing of the first arm assembly along a first axis. In addition, the elongate member of the second arm assembly may be rotatable about the first axis.

In an embodiment, the elongate member of the second arm assembly may be rotatable about a second axis defined by the engagement housing of the first arm assembly.

In still yet another embodiment, the elongate member of the second arm assembly may be rotatable about an axis offset from the second axis defined by the engagement housing of the first arm assembly.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION

Figure 1:
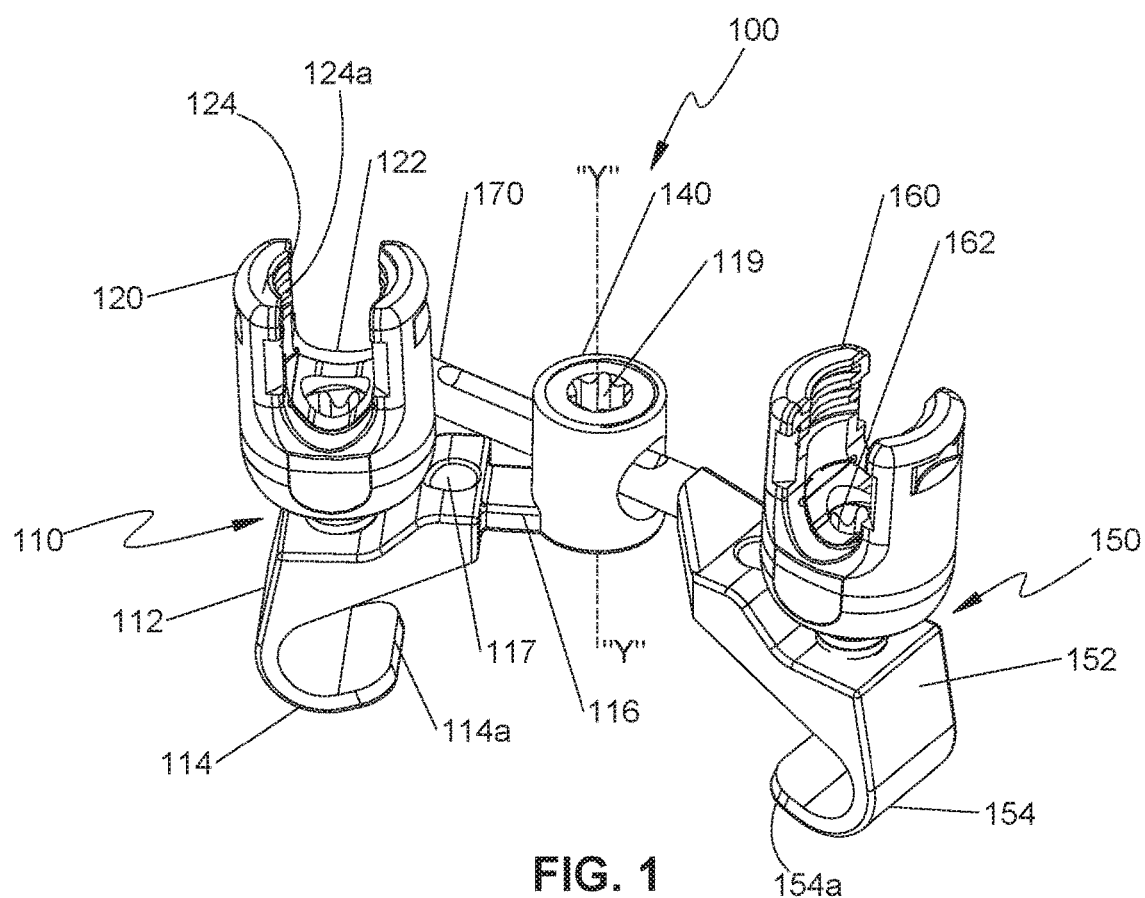
FIG. 1 is a perspective view of a transverse connector in accordance with an embodiment of the present disclosure.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" is used in this application to indicate a direction towards a patient's head, whereas the term "caudad" indicates a direction towards the patient's feet. Further still, the term "medial" indicates a direction towards the middle of the body of the patient, while the term "lateral" indicates a direction towards a side of the body of the patient (i.e., away from the middle of the body of the patient). The term "posterior" indicates a direction towards the patient's back, and the term "anterior" indicates a direction towards the patient's front. In the following description, well-known functions or constructions are not described in detail to avoid obscuring the present disclosure in unnecessary detail.

Figure 2:
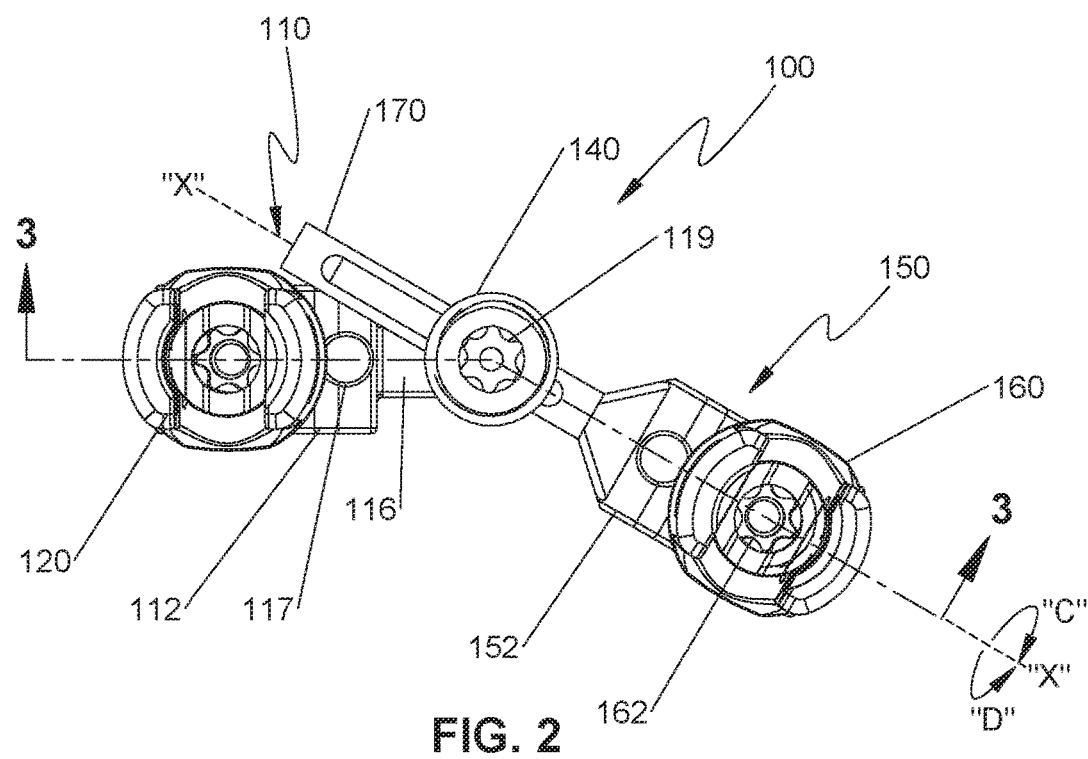
FIG. 2 is a top view of the transverse connector of FIG. 1.
Figure 10:
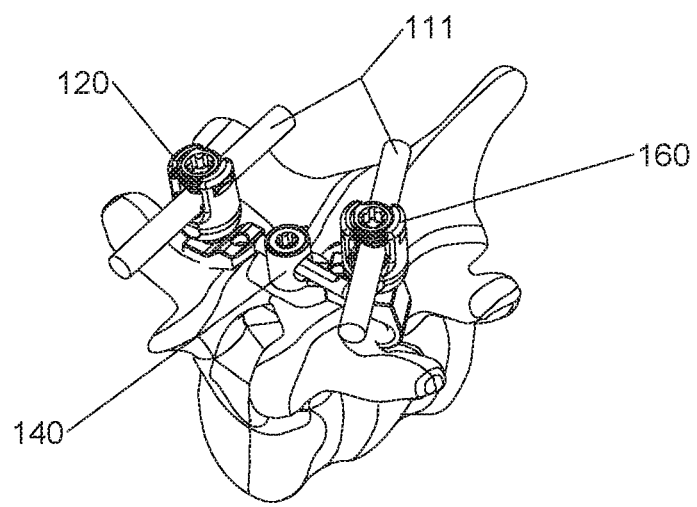
FIG. 10 is a perspective view of the transverse connector of FIG. 1, illustrating use with spinal rods.

With reference to FIGS. 1-2, a transverse connector in accordance with an embodiment of the present disclosure is generally shown as a transverse connector 100. Transverse connector 100 is configured to secure spinal rods 111 (FIG. 10) to inhibit relative movement of the spinal rods 111 in order to maintain the desired relative positions of the spinal construct and therefore the associated vertebrae. The transverse connector 100 may be secured to, e.g., the pars interarticularis ("pars") or articular process of a vertebra. The transverse connector 100 includes a first arm assembly 110 and a second arm assembly 150 adjustably coupled with the first arm assembly 110 to selectively adjust relative position and orientation of the first and second arm assemblies 110, 150 in order to ensure a secure fit across the pars or articular process. The second arm assembly 150 is movable relative to an engagement housing 140 of the first arm assembly 110 along a first axis "X-X" (FIG. 2) to adjust the relative distance therebetween and rotatable about the first axis "X-X" in a first direction "C" or a second direction "D". In addition, the second arm assembly 150 is rotatable about a second axis "Y-Y" (FIG. 1) defined by the engagement housing 140 and axes offset from the second axis "Y-Y" to effect poly-axial rotation. Under such a configuration, the first and second arm assemblies 110, 150 may define an angle of about 180°. Alternatively, the first and second arm assemblies 110, 150 may define an angle less than about 170°. In an embodiment, the first and second arm assemblies 110, 150 may define an angle less than about 160°.

The first arm assembly 110 includes a first base portion 112 and a first head portion 120 rotatably coupled with the first base portion 112. The first base portion 112 includes a first hook 114 configured to engage an anatomical structure of the vertebra such as, e.g., the pars or articular process, and an extension member 116 including the engagement housing 140. The first hook 114 may include a beveled edge 114a configured to abut or cut into the bony tissue in order to provide a friction fit or tight fit of the transverse connector 100. The first base portion 112 defines an engagement bore 117 dimensioned to engage an insertion instrument 200 (FIG. 5), as will be described below.

Figure 3:
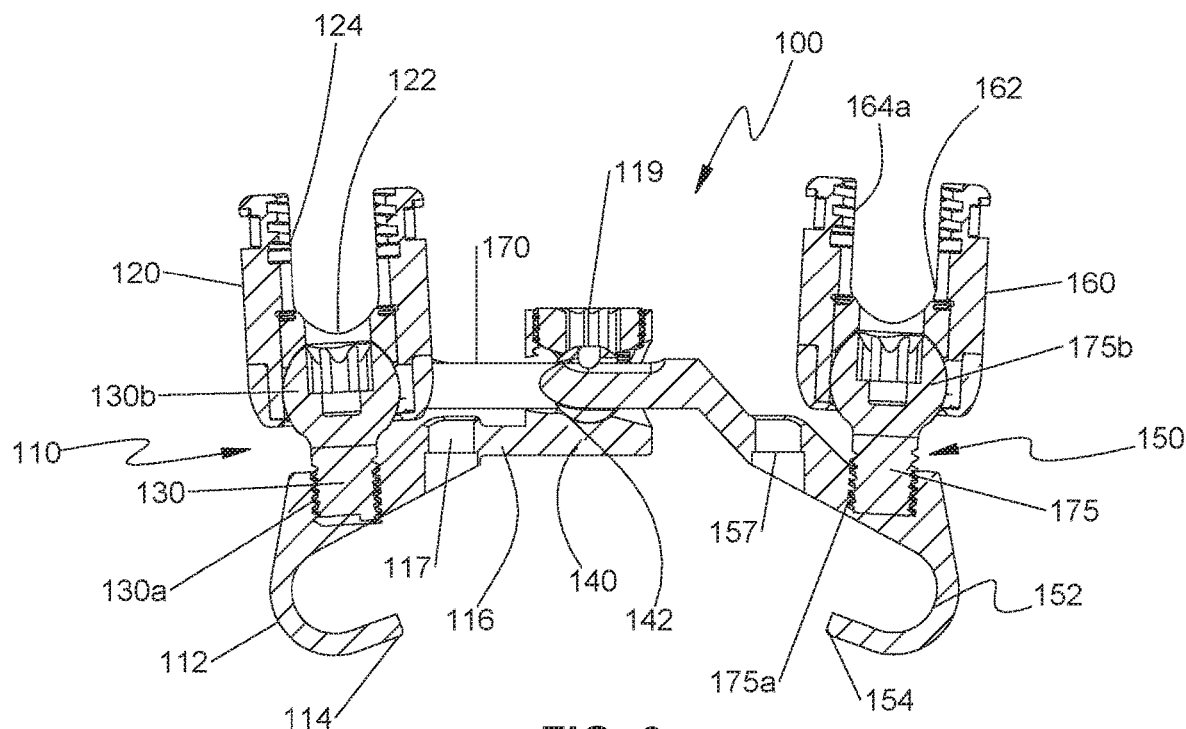
FIG. 3 is a cross-sectional view taken along section line 3-3 of FIG. 2.
Figure 4:
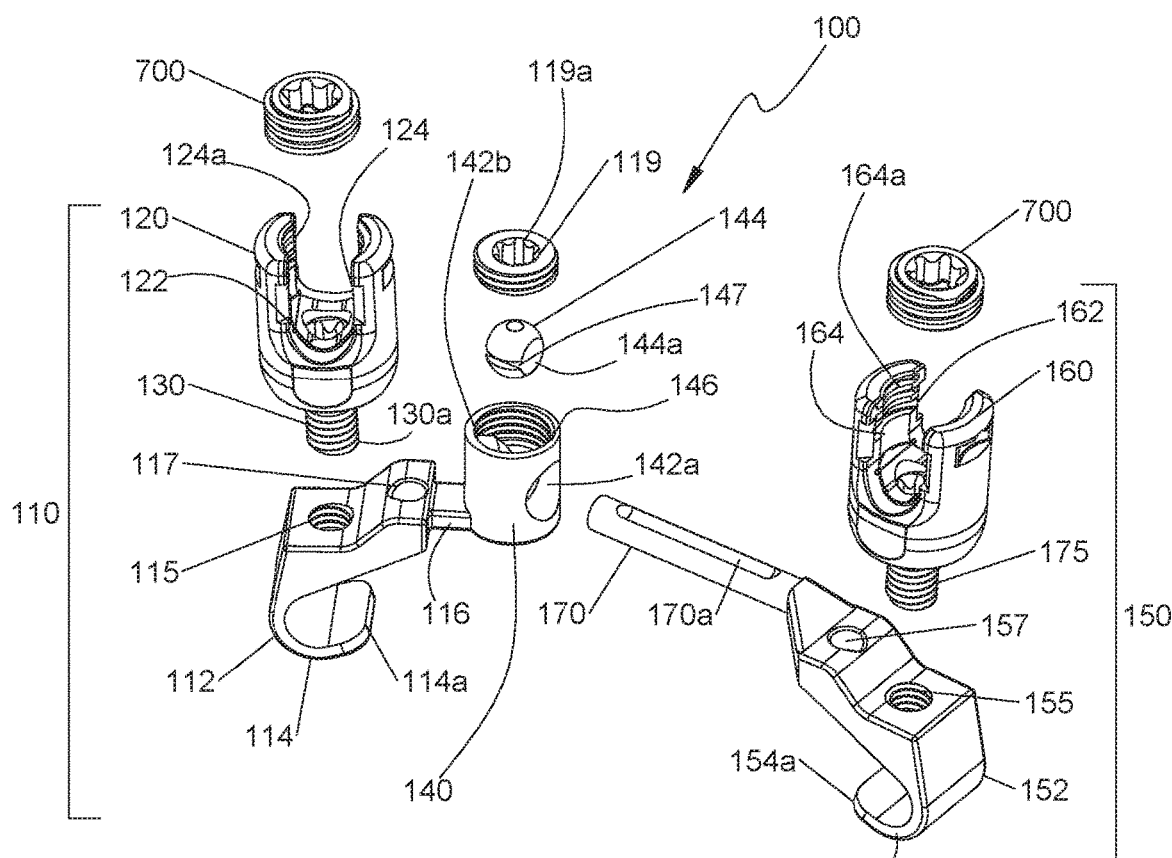
FIG. 4 is an exploded, perspective view of the transverse connector of FIG. 1 with parts separated.

With reference now to FIGS. 3 and 4, the first head portion 120 is coupled with the first base portion 112 by a first stem 130. The first stem 130 includes a threaded portion 130a threadably coupled with a threaded bore 115 defined in the first base portion 112, and a ball 130b rotatably coupled with the first head portion 120 to enable poly-axial rotation of the first head portion 120 relative to the first base portion 112. It is contemplated that the threaded bore 115 may be in communication with the first hook 114 such that the first stem 130 may be selectively threaded into threaded bore 115 in order to engage an anatomical structure, such as, e.g., the pars or the articular process, of the vertebra disposed on the first hook 114 to further enhance securement of the transverse connector 100 on the vertebrae.

The first head portion 120 defines a first slot 122 having a U-shaped profile configured to receive the spinal rod 111 (FIG. 10) therein. An inner wall 124 of the first head portion 120 includes threads 124a configured to threadably receive a set screw 700 to secure the spinal rod 111 in the first slot 122. Reference may be made to U.S. Pat. Nos. 5,683,392; 5,733,286; 7,658,582; 7,717,940; 7,771,430; 7,988,694; 8,113,847; 8,162,991; 8,287,576; 8,308,729; 8,361,122; 8,377,104; 8,403,971; 8,506,603; 8,672,944; 8,696,718; 8,714,427; 8,764,756; 8,814,919; 8,834,474; 8,882,817; 8,945,189; 8,961,523; 8,979,898; 9,125,703; RE42,867; and 9,247,969, the entire contents of each of which is incorporated herein by reference, for a detailed description of the construction and operation of a head portion and a stem.

With continued reference to FIGS. 3 and 4, the extension member 116 of the first base portion 112 extends from the first hook 114 and includes the engagement housing 140. The engagement housing 140 defines a ball socket 142 that receives a ball 144 therein. The engagement housing 140 further defines first and second transverse openings 142a, 142b in communication with a bore 144a defined in the ball 144 disposed in the ball socket 142 to selectively receive an elongate member 170 of the second arm assembly 150 therethrough. The first and second transverse openings 142a, 142b may be dimensioned to provide a suitable multi-axial rotation of the elongate member 170 relative to the engagement housing 140. Specifically, the first and second transverse openings 142a, 142b may include dimensions larger than a diameter of the elongate member 170 to provide a greater degree of rotation of the elongate member 170 relative to the engagement housing 140. For example, the first and second transverse openings 142a, 142b may be outwardly tapered or may include a conical profile to enable multi-directional and/or multi-planar rotation of the elongate member 170 relative to the engagement housing 140.

With particular reference to FIG. 4, the ball 144 defines a slit 147 to enable compression of the ball 144 against the elongate member 170 of the second arm assembly 150. The engagement housing 140 further defines a screw opening 146 configured to threadably receive the set screw 119. The screw opening 146 is in registration with the ball 144 disposed in the ball socket 142. The set screw 119 is threadably received in the engagement housing 140 and directly engages the ball 144 to apply compression to the ball 144, which, in turn, secures the elongate member 170 with the ball 144 and the ball 144 with the ball socket 142. In this manner, the fastening of the set screw 119 secures the relative position and orientation of the elongate member 170 with respect to the engagement housing 140.

With reference to FIGS. 3 and 4, the second arm assembly 150 includes a second base portion 152 and a second head portion 160. The second base portion 152 includes a second hook 154 configured to engage an anatomical structure of the vertebra such as, e.g., the pars or articular process of a vertebra, and the elongate member 170. The second hook 154 may include a beveled edge 154a configured to abut or cut into the bony tissue to provide a friction fit or tight fit of the transverse connector 100. The second base portion 152 defines an engagement bore 157 dimensioned to receive the insertion instrument 200 (FIG. 5), as will be described below.

The second head portion 160 defines a second slot 162 having a U-shaped profile configured to receive the spinal rod 111 (FIG. 10) therein. An inner wall 164 of the second head portion 160 includes threads 164a configured to receive a set screw 700 to secure the spinal rod 111 in the second slot 162. The second head portion 160 is rotatably coupled with the second base portion 152 by a second stem 175. In particular, the second stem 175 includes a threaded portion 175a threadably coupled with a threaded bore 155 of the second base portion 152, and a ball 175b rotatably coupled with the second head portion 160 to enable polyaxial rotation of the second head portion 160 relative to the second base portion 152.

The elongate member 170 of the second base portion 152 extends from the second hook 154. The elongate member 170 defines, e.g., a cylindrical profile. The elongate member 170 may include a cutout 170a including a planar surface to enhance securement with the ball 144 when the ball 144 is compressed by the set screw 119. As discussed hereinabove, the elongate member 170 is configured to be received through the bore 144a of the ball 144 and the transverse openings 142a, 142b of the engagement housing 140 of the first arm assembly 110. The elongate member 170 is slidable through the ball 144, and thus the set screw 119 is securable in any one position of a plurality of positions along the elongate member 170. Furthermore, the elongate member 170 is also rotatable about the first axis "X-X" (FIG. 2). In addition, the elongate member 170 is rotatable about the second axis "Y-Y" (FIG. 1) transverse to the first axis "X-X" (FIG. 2) defined by the elongate member 170, and axes offset from the second axis "Y-Y".

Figure 5:
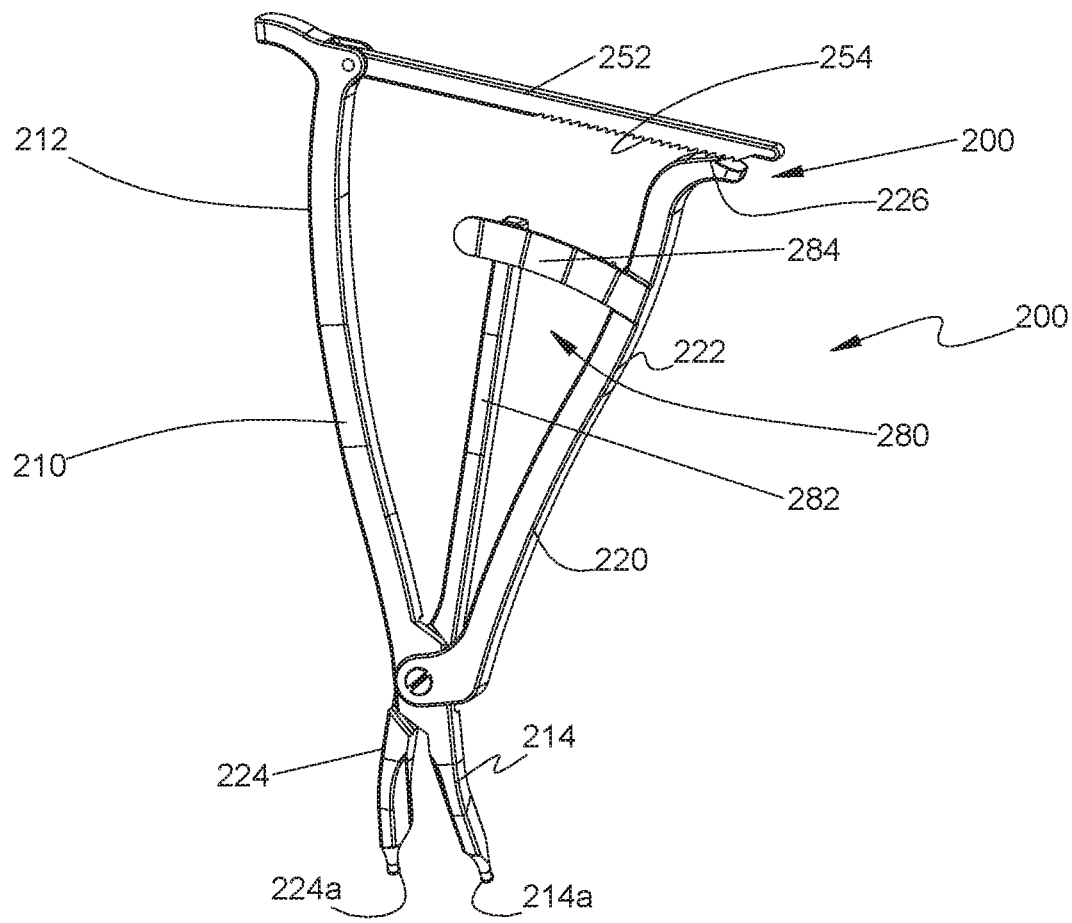
FIG. 5 is a perspective view of an insertion instrument for use with the transverse connector of FIG. 1.
Figure 6:
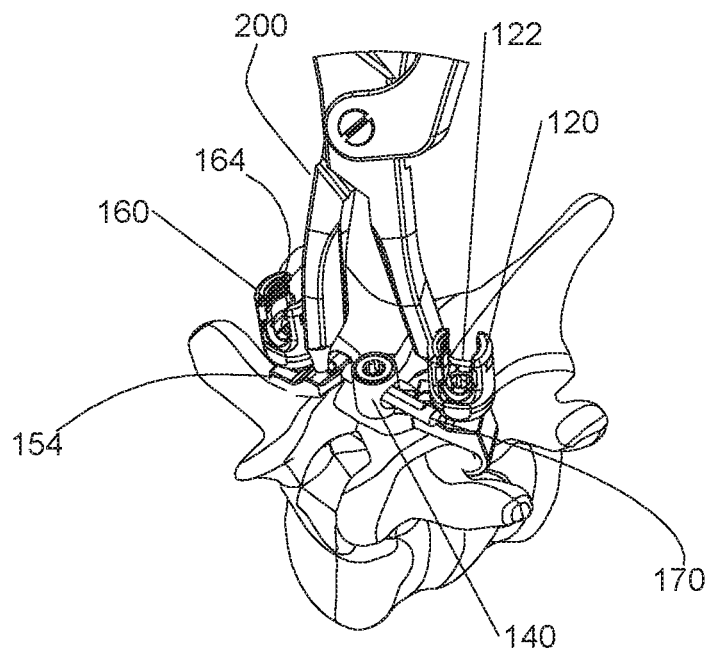
FIG. 6 is a partial, perspective view the insertion instrument of FIG. 5, illustrating use with the transverse connector of FIG. 1.

With reference now to FIGS. 5 and 6, the insertion device 200 is utilized to place the transverse connector 100 at the surgical site. In particular, the insertion device 200 includes first and second members 210, 220 pivotally coupled to each other. The first member 210 includes a first handle portion 212 and a first engaging portion 214. The first engaging portion 214 includes a distal end 214a configured to engage one of the engagement bores 117, 157 (FIG. 4) of the first and second arm assemblies 110, 150 of the transverse connector 100. Similarly, the second member 220 includes a second handle portion 222 and a second engaging portion 224. The second engaging portion 224 includes a distal end 224a configured to engage the other one of the engagement bores 117, 157 (FIG. 4) of the first and second arm assemblies 110, 150 of the transverse connector 100.

When the first and second handle portions 212, 222 are squeezed together, the distal ends 214a, 224a of the first and second engaging portions 214, 224 are spread apart to securely engage the respective engagement bores 117, 157 of the first and second arm assemblies 110, 150. The first and second members 210, 220 further include a locking ratchet 250 configured to maintain the relative position of the first and second handle portions 212, 222, while enabling further squeezing of the first and second handle portions 212, 222. In particular, the locking ratchet 250 includes a rack 252 pivotally connected to the first handle portion 212. The rack 252 includes teeth 254 extending along a length of the rack 252. The second handle portion 222 includes a tooth 226 configured to engage the teeth 254 of the rack 252.

The first and second engaging portions 214, 224 of the first and second members 210, 220 of the insertion device 200 are offset from respective axes defined by the first and second handle portions 212, 222. Under such a configuration, the first and second handle portions 212, 222 define an angle with the driver 300 (FIG. 9) during use such that manipulation of the first and second handle portions 212, 222 of the insertion device 200 does not obstruct or interfere with any of the functions of the driver 300 or vice versa.

With continued reference to FIGS. 5 and 6, the insertion device 200 further includes a compression indicator 280 configured to provide tactile indication of the amount of force applied to the first and second arm assemblies 110, 150 of the transverse connector 100. In particular, the compression indicator 280 includes an elongate member 282 extending from the first engaging portion 214 of the first member 210 such that the elongate member 282 is interposed between the first and second handle portions 212, 222. The compression indicator 280 further includes an extension member 284 extending transversely from the second handle portion 222. The extension member 284 includes tactile notches (not shown) that operatively engage the elongate member 282 to indicate to the clinician the amount of force applied to the first and second arm assemblies 110, 150 of the transverse connector 100.

Figure 7:
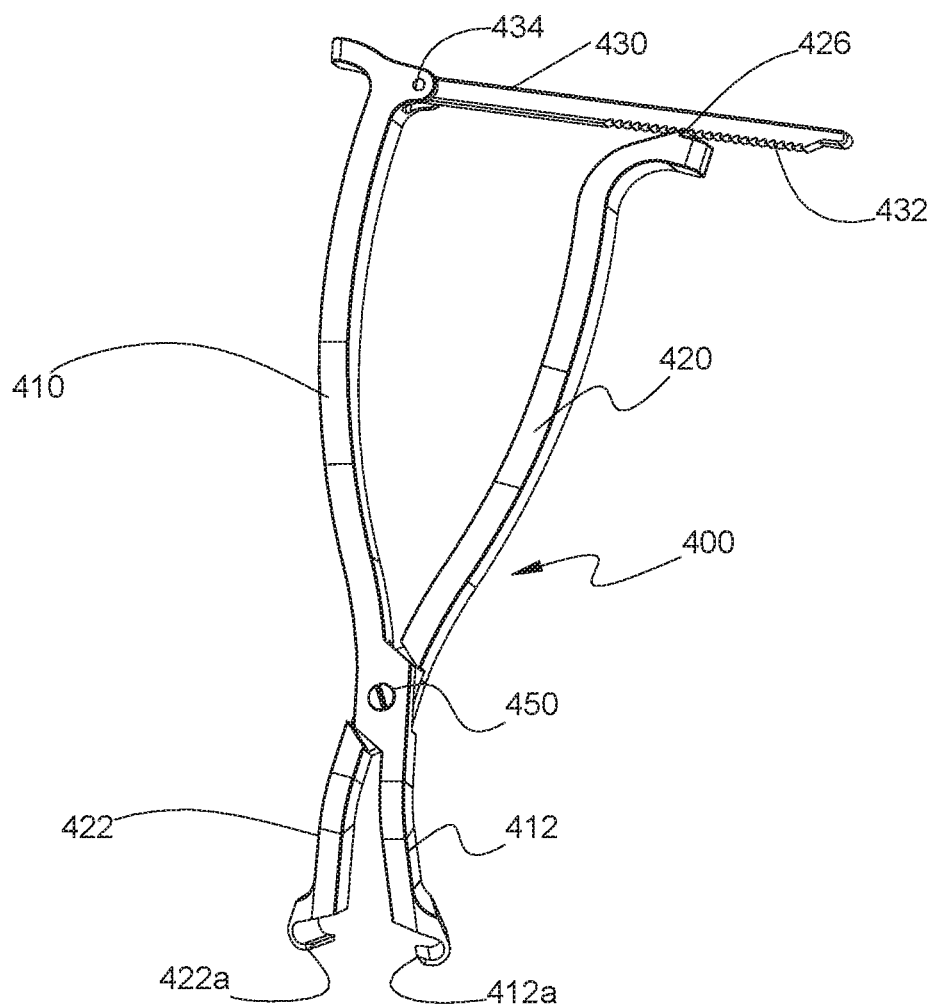
FIG. 7 is a perspective view a preparation instrument for use with the transverse connector.
Figure 8:
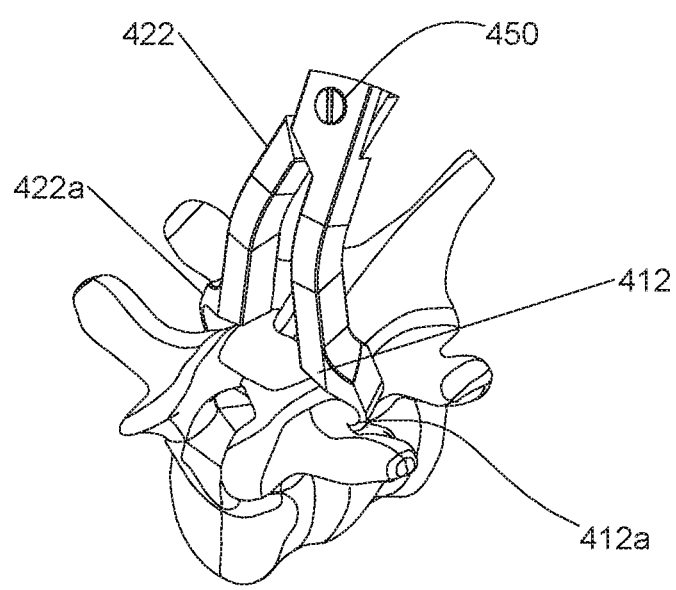
FIG. 8 is a partial, perspective view of the preparation instrument of FIG. 7 coupled to a vertebra.

With reference now to FIGS. 7 and 8, a preparation tool 400 may be utilized to prepare, e.g., the pars or articular process of a vertebra. The preparation tool 400 includes first and second arms 410, 420 pivotally coupled about a pivot 450. The first arm 410 includes a first engaging portion 412 including a first hook portion 412a, and the second arm 420 includes a second engaging portion 422 including a second hook portion 422a. The first and second hook portions 412a, 422a may be similar to the first and second hooks 114, 154 (FIG. 1) of the first and second arm assemblies 110, 150 of the transverse connector 100. The first and second hook portions 412a, 422a may include an angled edge configured to clear tissue from the vertebra. The preparation tool 400 further includes a ratchet arm 430 pivotably attached to the first arm 410 about a pivot 434. The ratchet arm 430 includes teeth 432 configured to engage a tooth 426 extending from the second arm 420. Under such a configuration, the ratchet arm 430 may easily transition between a locking state, in which, the ratchet arm 430 maintains the relative position of the first and second arms 410, 420 and a released state, in which, the first and second arms 410, 420 are freely movable relative to each other.

Figure 9:
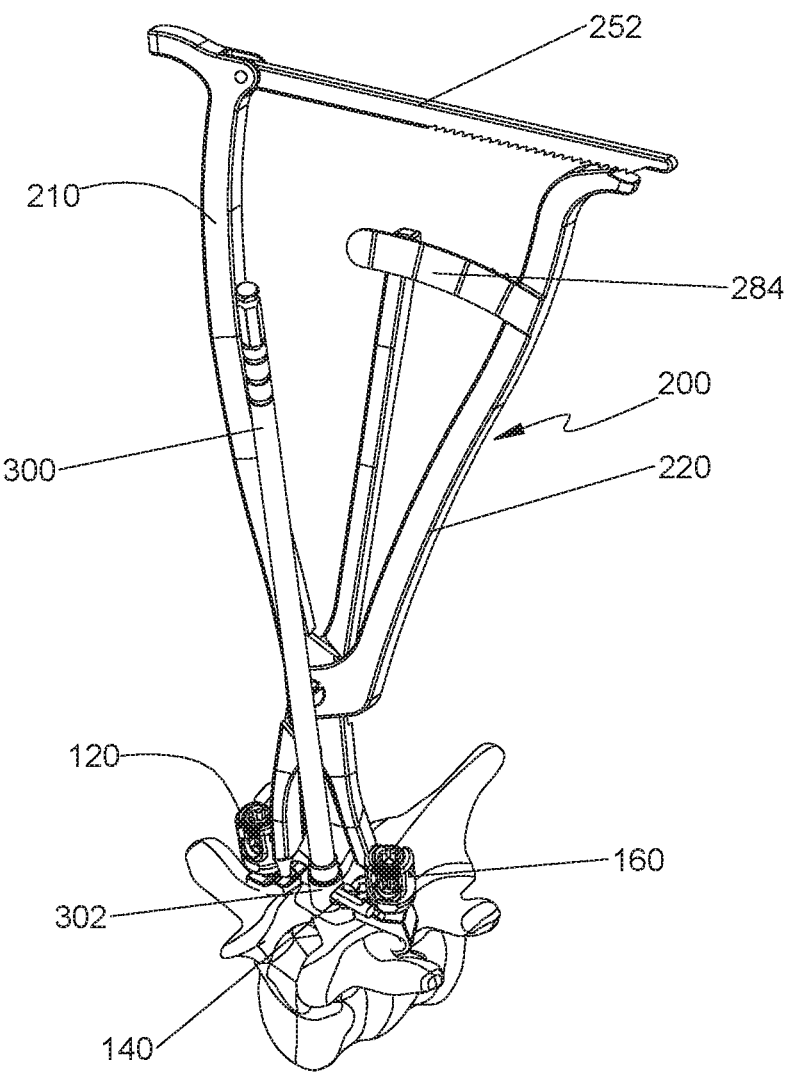
FIG. 9 is a perspective view of the insertion instrument of FIG. 5 and a driver for use with the transverse connector of FIG. 1, illustrating use with the transverse connector.

With reference now to FIG. 9, the driver 300 is utilized to control the insertion and/or advancement of the set screw 119 (FIG. 1) into and/or out of the engagement housing 140 of the first arm assembly 110 by threadably rotating the set screw 119 in the screw opening 146 (FIG. 4) of the engagement housing 140 of the transverse connector 100. The set screw 119 defines a recess 119a (FIG. 4) configured to mate with the driver 300. The recess 119a has a hex feature complementary with an engaging portion 302 of the driver 300 to enable the driver 300 to control the insertion and/or advancement of the set screw 119 into the engagement housing 140. The set screw 119 is threadably inserted into the screw opening 146 of the engagement housing 140 of the first arm assembly 110 to directly engage the ball 144 (FIG. 4) in order to secure the relative position and orientation of the elongate member 170 of the second arm assembly 150 with respect to the engagement housing 140 of the first arm assembly 110.

In use, the clinician initially prepares the vertebra utilizing the preparation tool 400. The clinician inserts the preparation tool 400 around the anatomical structure such as, e.g., the pars or articular process of a vertebra. The preparation tool 400 is inserted until the first and second hook portions 412a, 422a are placed under the pars or articular process. Once the first and second arms 410, 420 are pressed to fit around the pars or articular process, the ratchet arm 430 can engage the tooth 426 on the second arm 420 to inhibit the first and second hook portions 412a, 422a from moving apart. The transverse connector 100 may be expected to fit around the pars or articular process of the vertebra so long as the preparation tool 400 is able to fit around the pars or articular process. Once the tissue has been removed from the pars or articular process, the preparation tool 400 can be removed.

Bone anchors (not shown) are positioned at desired locations on the spine in order to provide the desired placement and securement of the spinal rods 111. Reference may be made to U.S. Patent Application Publication No. 2009/0292308, the entire contents of which is incorporated herein by reference, for a detailed description of the construction and operation of the bone anchor. Thereafter, the insertion device 200 is adjusted such that the distal ends 214a, 224a are received in the respective engagement bores 117, 157 of the first and second arm assemblies 110, 150 of the transverse connector 100. Once the distal ends 214a, 224a are inserted into the respective engagement bores 117, 157, the first and second handle portions 212, 222 are further squeezed to ensure secure engagement of the insertion device 200 with the transverse connector 100, while utilizing the compression indicator 280. In this manner, the transverse connector 100 is securely held by the insertion device 200 and can be placed at the surgical site. The transverse connector 100 is placed across the pars or articular process. The clinician may apply a force that separates distal end 214a, 224a from each other thereby adjusting the rotation and angulation of the first arm assembly 110 relative to the second arm assembly 150. This adjustment enables the clinician to place the beveled edges 114a, 154a of the first and second hooks 114, 154 around an underside of the pars or articular process.

After the first and second hooks 114, 154 are positioned to engage the pars or articular process of a vertebra, the spinal rods 111 are received in the respective first and second slots 122, 162 of the first and second head portions 120, 160 of the transverse connector 100. At this time, further adjustment to the first and second arm assemblies 110, 150 may be made. Upon achieving the desired placement of the transverse connector 100, the driver 300 is utilized to advance the set screw 119 in the engagement housing 140 to directly engage the ball 144 in order to secure the elongate member 170 with the engagement housing 140. During the use of the driver 300, the insertion device 200 maintains engagement with the first and second head portions 120, 160 and provides counter rotation to the engagement housing 140. Thereafter, the set screws 700 are used to secure the spinal rods 111 in the first and second slots 122, 162 of the first and second head portions 120, 160 and the bone anchors.

Figure 11:
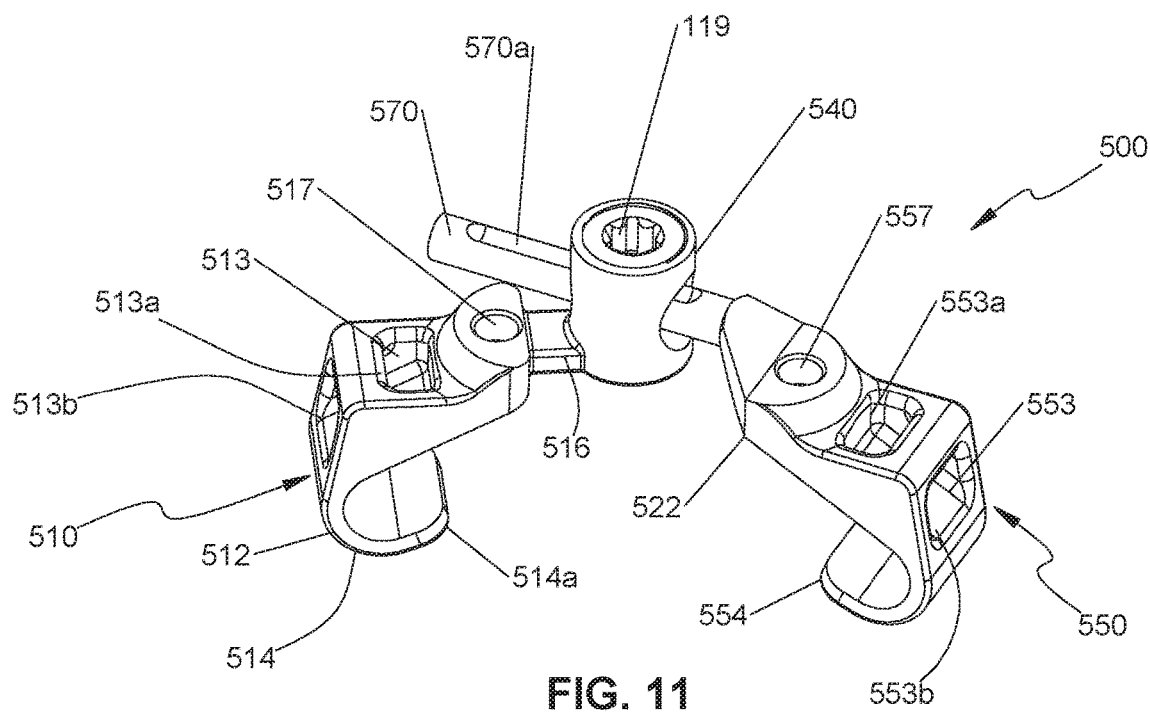
FIG. 11 is a perspective view of a transverse connector in accordance with another embodiment of the present disclosure.

With reference now to FIG. 11, there is illustrated a transverse connector 500 in accordance with another embodiment of the present disclosure. The transverse connector 500 includes features that are identical to the features described with respect to the transverse connector 100. Thus, the identical parts in the transverse connector 500 will not be described herein to avoid obscuring the present disclosure in unnecessary detail.

As discussed hereinabove with respect to the transverse connector 100, the transverse connector 500 is configured to secure spinal rods 111 (FIG. 15) to inhibit relative movement of the spinal rods 111 in order to maintain the desired relative positions of the spinal construct and therefore the associated vertebrae. The transverse connector 500 may be secured to an anatomical structure of the vertebra such as, e.g., the pars or articular process of a vertebra. The transverse connector 500 includes a first arm assembly 510 and a second arm assembly 550 adjustably coupled with the first arm assembly 510 to selectively adjust relative position and orientation of the first and second arm assemblies 510, 550 in order to ensure a secure fit across the pars or articular process. The second arm assembly 550 is movable relative to the engagement housing 540 of the first arm assembly 510 along a first axis "Z-Z" (FIG. 12) to adjust the relative distance therebetween and rotatable about the first axis "Z-Z". In addition, the second arm assembly 550 is also rotatable about a second axis "V-V" (FIG. 13) extending through the engagement housing 540 and axes offset from the second axis "V-V" to effect multi-planar rotation. Under such a configuration, the first and second arm assemblies 510, 550 may define an angle of about 180°. Alternatively, the first and second arm assemblies 510, 550 may define an angle less than about 170°. In an embodiment, the first and second arm assemblies 510, 550 may define an angle less than about 160°.

Figure 12:
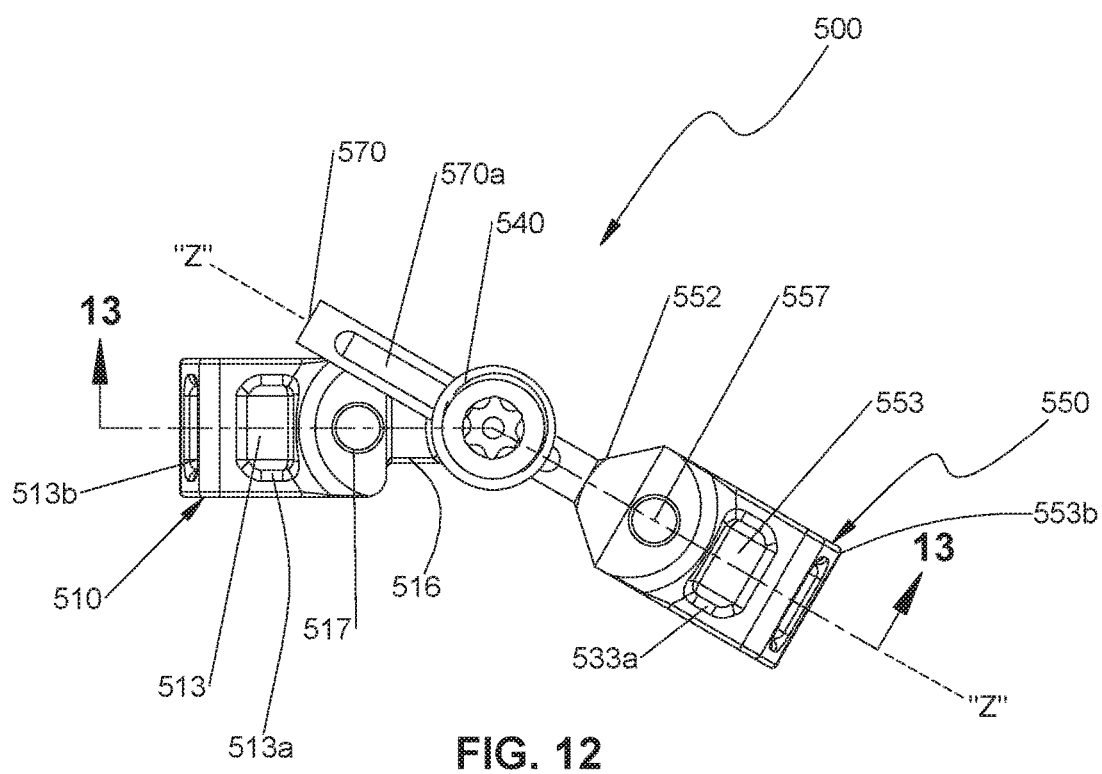
FIG. 12 is a top view of the transverse connector of FIG. 11.

With continued reference to FIGS. 11 and 12, the first arm assembly 510 includes a first base portion 512 including a first hook 514 configured to engage an anatomical structure of the vertebra such as, e.g., pars or articular process, and an extension member 516 including an engagement housing 540. The first hook 514 may include a beveled edge 514a configured to abut or cut into the bony tissue to provide a friction fit or tight fit of the transverse connector 500.

With continued reference to FIGS. 11 and 12, the first arm assembly 510 defines a fixation channel 513 configured to receive a band 600 (FIG. 15) therethrough. The band 600 may tightly secure the rod 111 to the first arm assembly 510 or enable slidable engagement with the rod 111. For example, a band clamp 800 (FIG. 15) may be utilized to clamp the opposite end portions of the band 600 together. The band clamp 800 defines a transverse bore 802 configured to receive the opposite end portions of the band 600, and a screw opening 804 configured to threadably receive a screw (not shown) therethrough. The screw opening 804 may be orthogonal to the transverse bore 802. In addition, the band clamp 800 includes an anvil (not shown) disposed in the transverse bore 802. The anvil is configured to compress, e.g., overlapping, opposite end portions of the band 600 disposed in the transverse bore 802. In particular, driving the screw through the screw opening 804 imparts a force on the anvil, which, in turn, compresses, e.g., overlapping, opposite end portions of the band 600, thereby clamping the opposite end portions of the band 600 together.

The fixation channel 513 includes openings 513a, 513b. For example, the openings 513a, 513b may be disposed orthogonal to each other. The size and shape of the openings 513a, 513b of the fixation channel 513 may be tailored to the shape and cross-section of the band 600. The first arm assembly 510 further defines an engagement bore 517 dimensioned to engage the insertion instrument 200 (FIG. 5). Reference may be made to U.S. Pat. No. 9,675,386 and U.S. Patent Application Publication No. 2014/0257397, the entire contents of each of which is incorporated herein by reference, for a detailed description of the construction and operation of the band 600.

Figure 13:
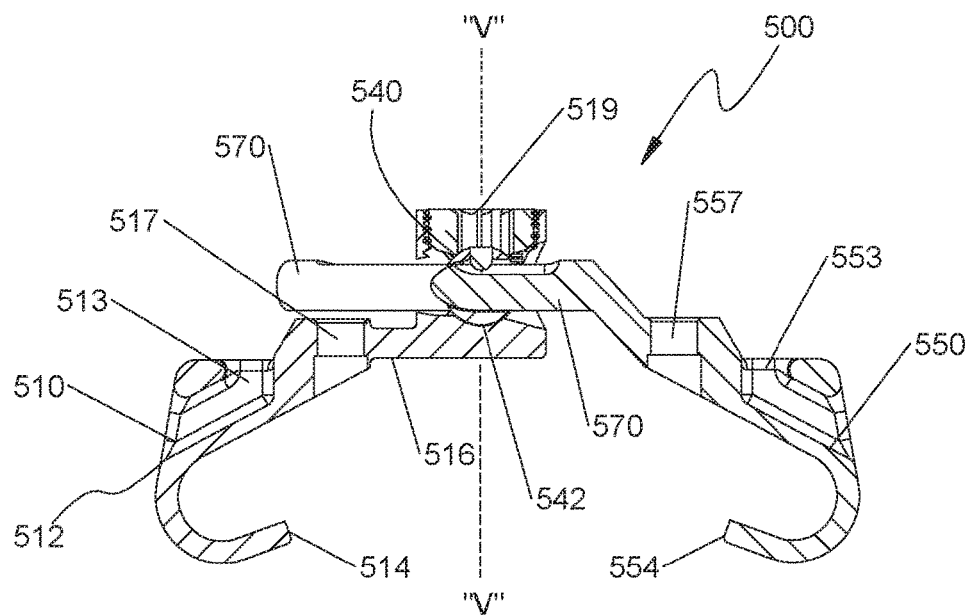
FIG. 13 is a cross-sectional view taken along section line 13-13 of FIG. 12.
Figure 14:
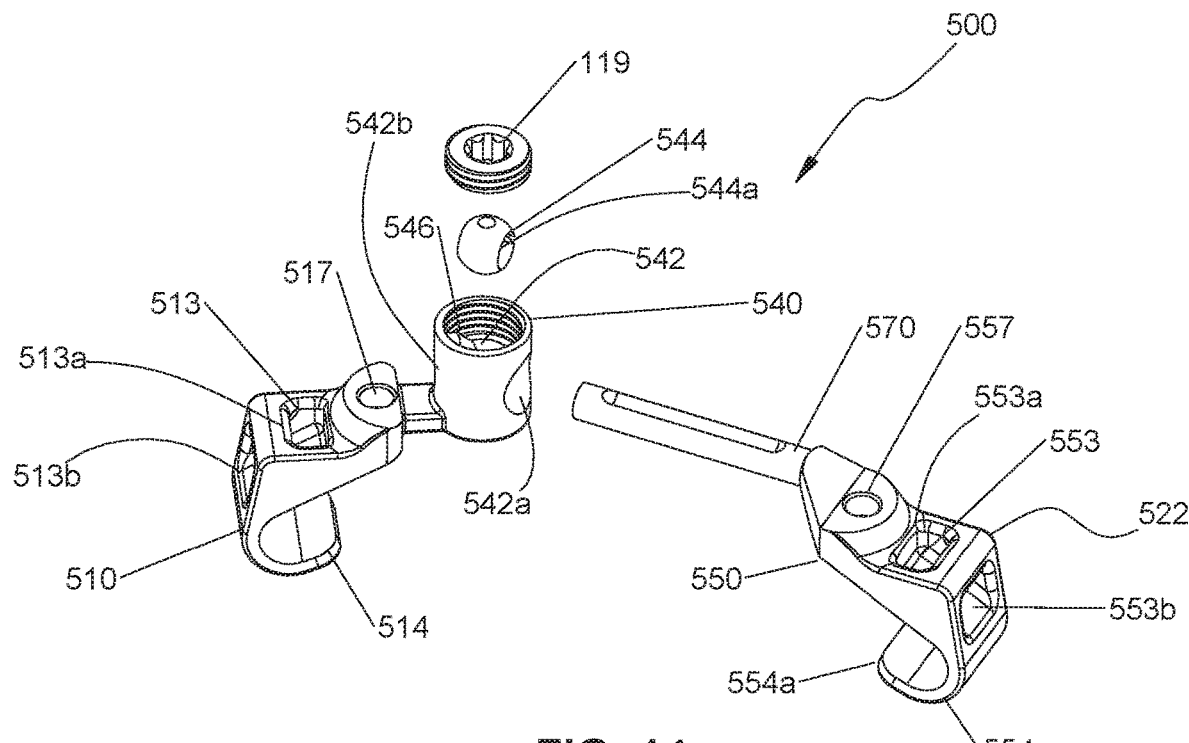
FIG. 14 is an exploded, perspective view of the transverse connector of FIG. 11 with parts separated.

With reference now to FIGS. 13 and 14, the extension member 516 of the first base portion 512 extends from the first hook 514 and includes the engagement housing 540. The engagement housing 540 defines a ball socket 542 configured to rotatably receive a ball 544 therein. The engagement housing 540 further defines first and second transverse openings 542a, 542b in communication with a bore 544a defined in the ball 544 disposed in the ball socket 542 to receive an elongate member 570 of the second arm assembly 550 therethrough. The first and second transverse openings 542a, 542b may include dimensions larger than a diameter of the elongate member 570 to provide a greater degree of rotation of the elongate member 570 relative to the engagement housing 540. For example, the first and second transverse openings 542a, 542b may include a conical profile to enable multi-directional and/or multi-planar rotation of the elongate member 570 relative to the engagement housing 540. The engagement housing 540 further defines a screw opening 546 configured to threadably receive the set screw 119. The screw opening 546 is in registration with the ball 544 disposed in the ball socket 542. The set screw 119 is threadably received in the engagement housing 540 and directly engages the ball 544 to apply compression to the ball 544, which, in turn, secures the elongate member 570 with the ball 544 and the ball 544 with the ball socket 542. In this manner, the fastening of the set screw 119 secures the relative position and orientation of the elongate member 570 with respect to the engagement housing 540.

With particular reference to FIG. 14, the second arm assembly 550 includes a second base portion 552 including a second hook 554 configured to engage an anatomical structure of the vertebra such as, e.g., the pars or articular process, and the elongate member 570. The second hook 554 may include a beveled edge 554a configured to abut or cut into the bony tissue to provide a friction fit or tight fit of the transverse connector 500. The second base portion 552 defines an engagement bore 557 dimensioned to receive the insertion instrument 200 (FIG. 5). The second arm assembly 550 defines a fixation channel 553 configured to receive the band 600 (FIG. 15) therethrough. In particular, the fixation channel 553 includes openings 553a, 553b. For example, openings 553a, 553b may be disposed orthogonal to each other. The size and shape of the openings 553a, 553b of the fixation channel 553 may be tailored to the shape and cross-section of the band 600.

The elongate member 570 of the second base portion 552 extends from the second hook 554. As discussed hereinabove, the elongate member 570 is configured to be received through the bore 544a of the ball 544 and the transverse openings 542a, 542b of the engagement housing 540 of the first arm assembly 510. The elongate member 570 is slidable through the ball 544, and thus the set screw 119 is securable in any one position of a plurality of positions along the elongate member 570. In addition, the elongate member 570 is rotatable about the second axis "V-V" (FIG. 13) of the engagement housing 540 and axes offset from the second axis "V-V" to enable poly-axial rotation.

Figure 15:
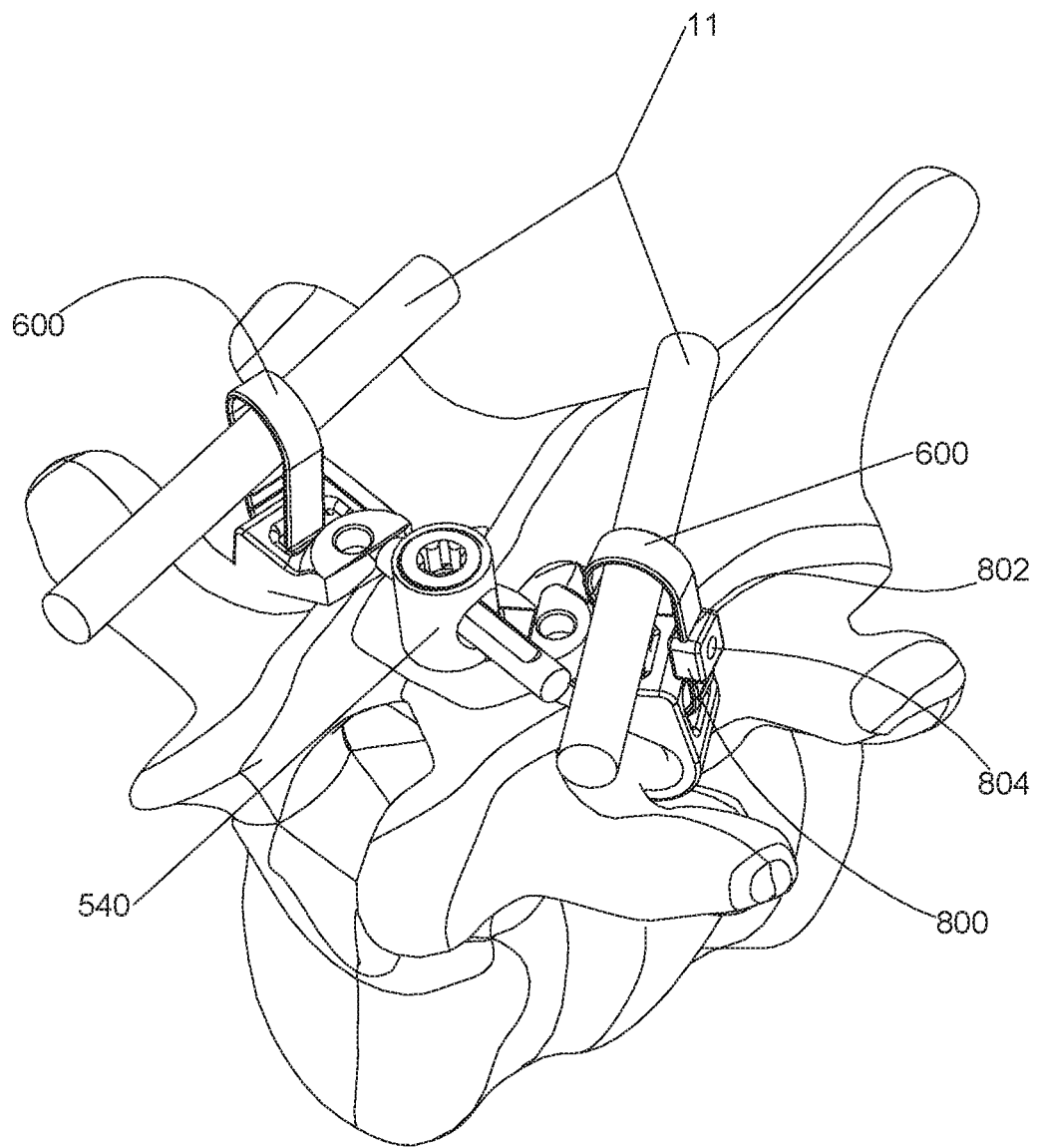
FIG. 15 is perspective view of the transverse connector of FIG. 11, illustrating use with spinal rods.

In use, the clinician initially prepares the vertebrae utilizing the preparation tool 400. Bone anchors (not shown) are positioned at desired locations on the spine in order to provide the desired placement and securement of the spinal rods 111 (FIG. 15). Thereafter, the insertion tool 200 is utilized to place the transverse connector 500 adjacent the surgical site. Specifically, the insertion device 200 is adjusted such that the distal ends 214a, 224a are received in the respective engagement bores 517, 557 of the transverse connector 500. The transverse connector 500 is then positioned adjacent the anatomical structure such as, e.g., the pars or articular process. The clinician may apply a force that separates the distal end 214a, 224a of the insertion device 200 from each other in order to adjust the position and orientation of the first arm assembly 510 relative to the second arm assembly 550. The transverse connector 500 is placed across the pars or articular process. The first and second hooks 514, 554 are positioned to engage the anatomical structure of the vertebra such as, e.g., the pars or articular process. Each band 600 is threaded through the respective fixation channel 513, 553 via the respective fixation openings 513a, 513b, 553a, 553b. The band 600 can tightly secure the rod 111 or enable slidable engagement with the rods 111 by utilizing the band clamp 800 (FIG. 15).

At this time, further adjustment to the first and second arm assemblies 510, 550 may be made. Upon achieving the desired placement of the transverse connector 500, the driver 300 is utilized to advance the set screw 119 in the engagement housing 540 to directly engage the ball 544 in order to secure the elongate member 570 relative to the engagement housing 540. During the use of the driver 300, the insertion device 200 maintains engagement with the first and second arm assemblies 510, 550 and provides counter rotation to the engagement housing 540. Thereafter, the set screws 700 are used to secure the spinal rods 111 in the bone anchors.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. For example, a transverse connector may include a first arm assembly having a head portion defining a slot to receive a spinal rod therein, and a second arm assembly defining a fixation channel configured to receive a band to secure a spinal rod to the second arm assembly. Therefore, the above description should not be construed as limiting, but merely as exemplifications of particular embodiments. Those skilled in the art will envision other modifications within the scope and spirit of the claims appended hereto.

What is claimed is:

1. A spinal rod connector comprising:
a first arm assembly including a first base portion and a first head portion defining a first slot configured to receive a first spinal rod therein, the first base portion including a hook portion and an extension member including an engagement housing, the extension member being monolithic with the first base portion;
a second arm assembly selectively adjustable with respect to the first arm assembly, the second arm assembly including a second base portion, a second head portion defining a second slot configured to receive a second spinal rod therein, and an elongate member extending from the second base portion, the second base portion including a hook portion, the elongate member configured to be selectively received in the engagement housing of the first arm assembly, the elongate member being monolithic with the second base portion; and
a fastener configured to be received in the engagement housing to secure the elongate member of the second arm assembly thereto.

2. The spinal rod connector according to claim 1, wherein the first arm assembly includes a stem configured to rotatably couple the first head portion with the first base portion.

3. The spinal rod connector according to claim 2, wherein the stem includes a threaded portion threadably engaging the first base portion, and a ball portion rotatably coupled with the first head portion.

4. The spinal rod connector according to claim 1, wherein the engagement housing of the first arm assembly defines apertures dimensioned to receive the elongate member of the second arm assembly.

5. The spinal rod connector according to claim 4, wherein the apertures of the engagement housing of the first arm assembly are dimensioned larger than a diameter of the elongate member.

6. The spinal rod connector according to claim 4, wherein the apertures of the engagement housing of the first arm assembly have a conical profile.

7. The spinal rod connector according to claim 1, wherein the engagement housing of the first arm assembly includes a ball defining a bore dimensioned to receive the elongate member of the second arm assembly.

8. The spinal rod connector according to claim 7, wherein the engagement housing defines an opening in registration with the ball, the opening configured to threadably receive the fastener, the fastener configured to engage the ball to secure the elongate member of the second arm assembly with the engagement housing.

9. The spinal rod connector according to claim 1, wherein the first and second base portions define engagement bores configured to engage an insertion instrument.

10. The spinal rod connector according to claim 1, wherein at least one of the first or second slots has a U-shaped profile.

11. The spinal rod connector according to claim 1, wherein at least one of the first or the second head portions is configured to threadably engage a set screw to secure the first or second spinal rod received in the first or second slot.

12. The spinal rod connector according to claim 1, wherein the elongate member is rotatable about an axis extending through the longitudinal axis of the engagement housing.

13. A spinal rod connector comprising:
a first arm assembly including a first base portion including a hook portion defining a first hook channel, the first base portion defining a first fixation channel dimensioned to receive a first band configured to secure a first spinal rod to the first base portion, the first fixation channel not in communication with the first hook channel, the first fixation channel being opposite the first hook channel from an end of the first hook portion;
a second arm assembly selectively adjustable with respect to the first arm assembly, the second arm assembly including a second base portion including a hook portion, the second base portion defining a second fixation channel dimensioned to receive a second band configured to secure a second spinal rod to the second base portion,
one of the first or second base portions having an extension member including an engagement member including an engagement housing, the other of the first or second base portions having an elongate member extending therefrom, the elongate member configured to be selectively received in the engagement housing; and
a fastener configured to be received in the engagement housing to secure the elongate member of the second arm assembly thereto.

14. The spinal rod connector according to claim 13, wherein at least one of the first or second base portions defines apertures in communication with the first or second fixation channel.

15. The spinal rod connector according to claim 14, wherein the apertures of the at least one of the first or second base portions are orthogonal to each other.

16. The spinal rod connector according to claim 13, wherein the first and second base portions define engagement bores configured to engage an insertion instrument.

17. The spinal rod connector according to claim 13, wherein the elongate member is movable through the engagement housing along a first axis.

18. The spinal rod connector according to claim 17, wherein the elongate member is rotatable about the first axis.

19. The spinal rod connector according to claim 17, wherein the elongate member is rotatable about a second axis defined by the engagement housing, the second axis being different than the first axis.

20. The spinal rod connector according to claim 19, wherein the elongate member is rotatable about an axis offset from the second axis defined by the engagement housing.

21. The spinal rod connector according to claim 13, wherein the engagement housing defines apertures dimensioned to receive the elongate member.

\* \* \* \* \*